United States Patent [19]
Hisada

[11] Patent Number: 5,876,392
[45] Date of Patent: Mar. 2, 1999

[54] DISPOSABLE ABSORBENT PANTS TYPE UNDERGARMENT WITH IMPROVED HEAT SEALED EDGES

[75] Inventor: Kenichi Hisada, Ehime-ken, Japan

[73] Assignee: Uni-Charm Corporation, Ehime-ken, Japan

[21] Appl. No.: 787,477

[22] Filed: Jan. 22, 1997

[30] Foreign Application Priority Data

Jan. 31, 1996 [JP] Japan .................................. 8-015995

[51] Int. Cl.⁶ .................................................. A61F 13/15
[52] U.S. Cl. ....................... 604/385.2; 604/392; 604/396
[58] Field of Search ............................. 604/385.1, 385.2, 604/392, 396, 393, 394

[56] References Cited

U.S. PATENT DOCUMENTS 5,449,353  9/1995  Watanebe et al. .................... 604/385.2

FOREIGN PATENT DOCUMENTS

| 0487921A | 6/1992 | European Pat. Off. . | |
| 4371147 | 12/1992 | Japan | 604/385.2 |
| 4371148 | 12/1992 | Japan | 604/385.2 |
| 7-44945 | 5/1995 | Japan . | |
| WO93/17648 | 9/1993 | WIPO . | |

*Primary Examiner*—Mark O. Polutta
*Attorney, Agent, or Firm*—Lowe Hauptman Gopstein Gilman & Berner

[57] ABSTRACT

A disposable absorbent pants type undergarment is provided on front and rear waist regions with a plurality of elastic members extending circumferentially parallel to one another and spaced apart one from another along a longitudinal axis of the undergarment so that, between each pair of adjacent elastic members provided on one of the front and rear waist regions, each elastic member provided on the other of the front and rear waist regions is interposed.

5 Claims, 4 Drawing Sheets

5,876,392

DISPOSABLE ABSORBENT PANTS TYPE UNDERGARMENT WITH IMPROVED HEAT SEALED EDGES

BACKGROUND OF THE INVENTION

The present invention relates generally to disposable absorbent pants type undergarments in the form of a disposable diaper, training pants, incontinence pants or the like.

Conventional disposable pants type diapers are generally provided along an edge of a waist-opening thereof with circumferentially extending elastic members. Specifically, Japanese Patent Publication Application No. Hei 7-44945 discloses a disposable diaper provided with a first group of elastic members extending circumferentially parallel one to another along edges of a waist-opening defined by front and rear waist regions thereof. In addition, on the front and rear waist regions between the first group and a crotch region thereof, there is provided a second group of elastic members extending circumferentially parallel to one another. In this known diaper, opposite side edges of the front and rear waist regions are joined together, respectively, to form the pants type diaper. Consequently the elastic members of the front and rear waist regions substantially overlap at the flat side edges thereof and are bonded together such that the respective circumferential lines of elasticity are continuous.

Locations of each side edge at which the elastic members of the front and rear waist regions overlap are substantially thicker than the remaining locations of the side edge and present the correspondingly high rigidity. As a result, the locations at which the elastic members of the front and rear waist regions overlap form protuberances which are relatively stiff and deteriorate touch of the diaper.

SUMMARY OF THE INVENTION

In view of the problem described above, it is a principal object of the invention to provide a disposable absorbent pants type undergarment provided on front and rear waist regions thereof with circumferentially extending elastic members arranged to eliminate a concern that the elastic members might deteriorate touch of the diaper particularly at transversely opposite side edges thereof.

The object set forth above is achieved, according to the invention by a disposable absorbent pants type undergarment having a front region, rear region and a crotch region therebetween. The undergarment comprises a liquid-permeable topsheet, a liquid-impermeable backsheet and a liquid-absorbent core disposed therebetween. The front and rear waist regions are laid flat with the topsheet being located inside and bonded together along transversely opposite side edges thereof to define a waist-opening and a pair of leg-openings provided with a plurality of elastic members extending circumferentially parallel one to another and spaced apart one from another along the longitudinal axis of the undergarment.

The elastic members are arranged such that between each pair of adjacent elastic members provided on one of the front and rear waist regions there is interposed each of the elastic members provided on the other of the front and rear waist regions.

The invention allows the side edges of the disposable pants type undergarment to be relatively soft and comfortable to touch even when the mutually facing side edges of the front and rear waist regions are flat and bonded together since the elastic members extending circumferentially on the front and rear waist regions alternate with one another without overlap. Consequently, the respective side edges of the front and rear waist regions define even and planar surfaces that enable the side edges to be joined together, for example, by the ultrasonic-seaming.

DESCRIPTION OF THE PREFERRED EMBODIMENTS

Figure 1:
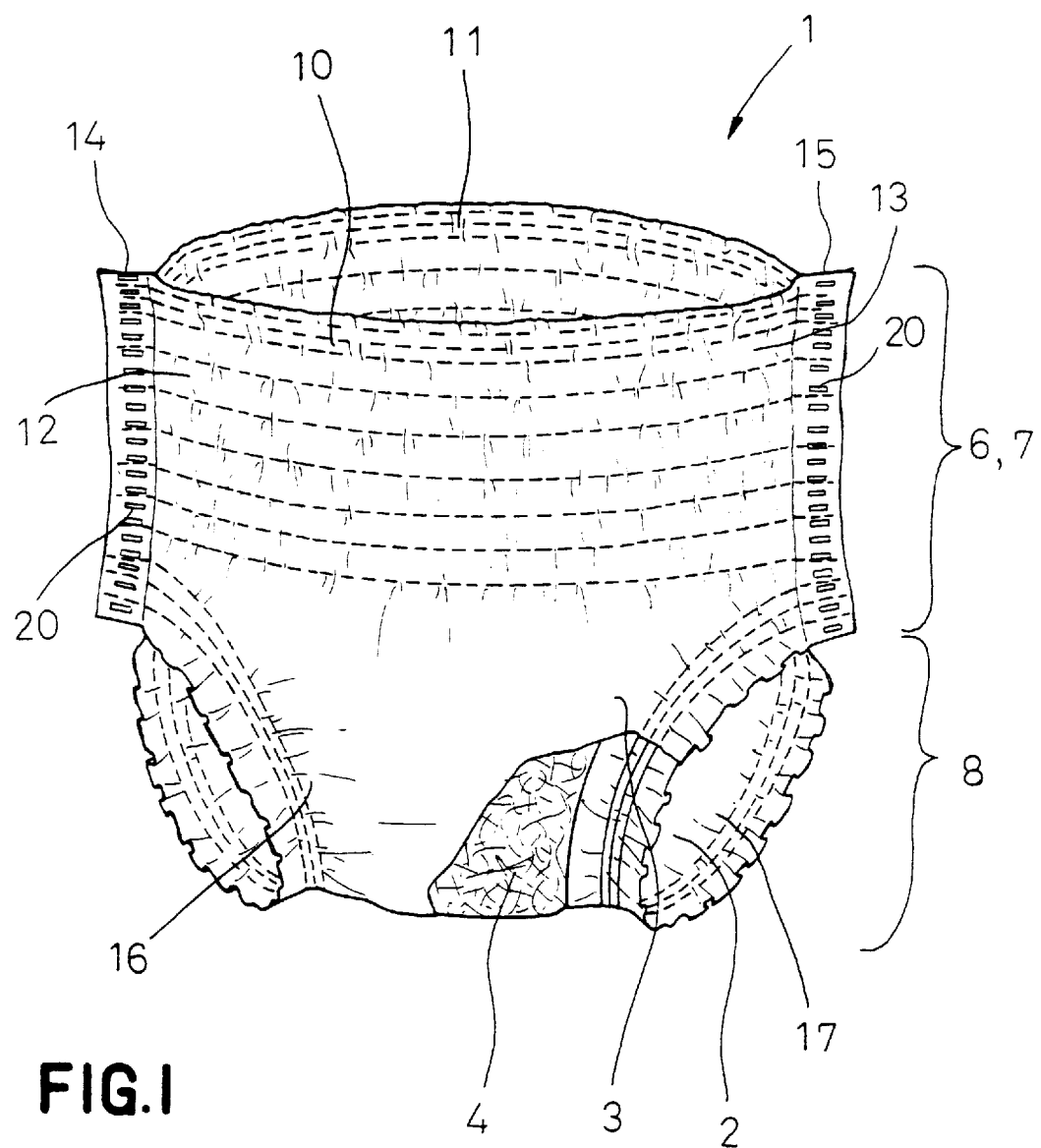
FIG. 1 is a perspective view showing the inventive undergarment (diaper) as partially broken away.
Figure 2:
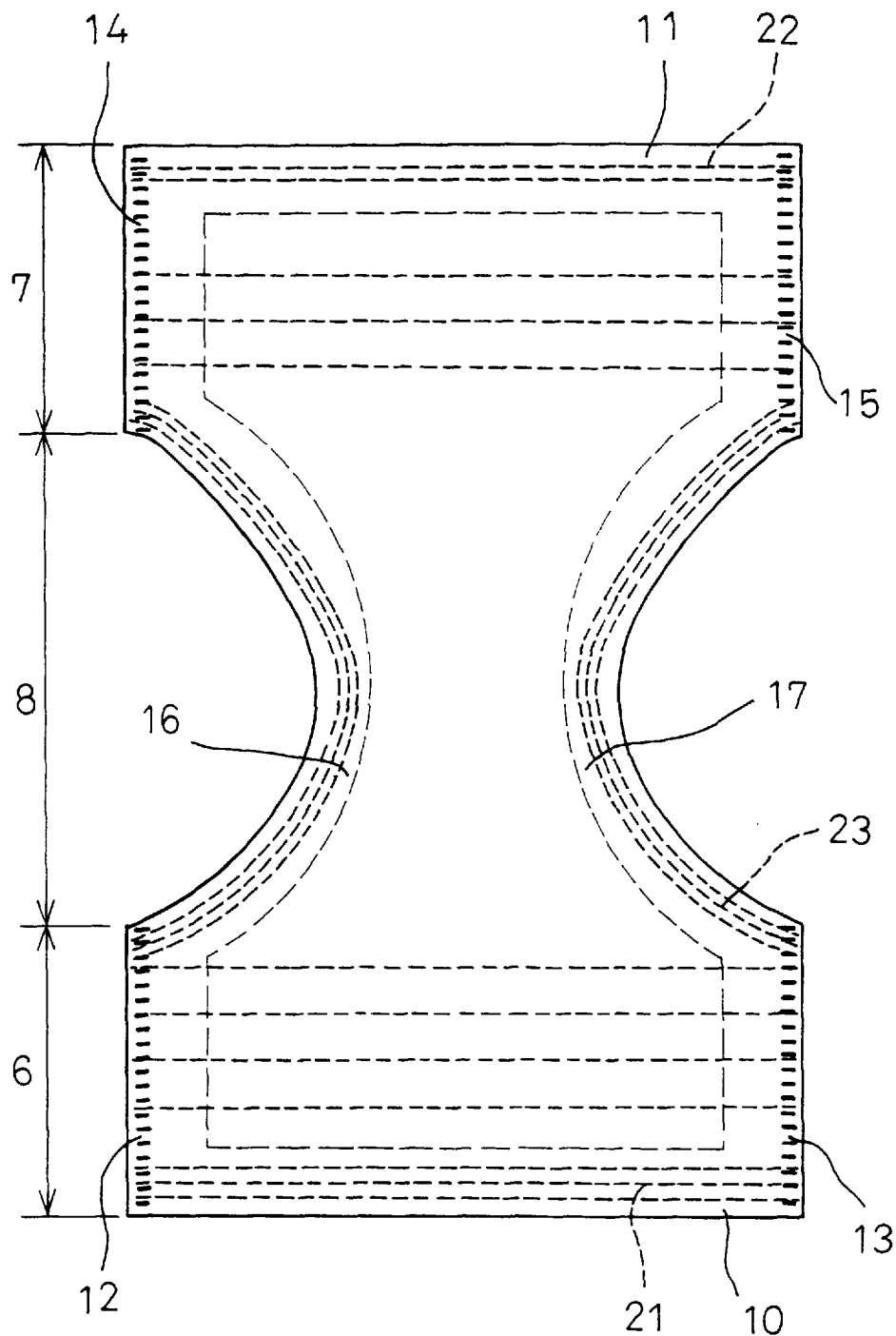
FIG. 2 is a plan view showing the diaper as developed longitudinally thereof.

FIGS. 1 and 2 respectively illustrate a pants type diaper 1 of the invention which has a front waist region 6, a rear waist region 7 and a crotch region 8 extending therebetween. The diaper 1 typically comprises a liquid-permeable topsheet 2, a liquid-impermeable backsheet 3 and a liquid-absorbent core 4 disposed therebetween. The topsheet 2 and the backsheet 3 are joined together along portions thereof extending outward beyond a peripheral edge of the core 4 to define longitudinally opposite ends 10, 11, transversely opposite side edges 12, 13; 14, 15 of the front and rear waist regions 6, 7 and a pair of inwardly curved edges 16, 17 in the crotch region 8 adapted to surround the wearer's legs.

Referring to FIG. 2, the front and rear waist regions 6, 7 respectively include a plurality of elastic members 21, 22 extending along the longitudinally opposite ends 10, 11 thereof and are spaced apart from one another longitudinally of the diaper 1. A plurality of elastic members 23, 23 extend along the respective inwardly curved edges 16, 17. The elastic members 21–23 are disposed between the topsheet 2 and the backsheet 3 or between the backsheet 3 an the core 4 so as to be secured to these two sheets 2, 3 or to the core 4. From the state shown by FIG. 2, the diaper 1 is folded in two with the topsheet 2 being located inside; then the respective side edges 12, 14 of the front and rear waist regions 6, 7 are ultrasonically-seamed to each other at intermittent spots 20 (See FIG. 1). Similarly, the respective side edges 13, 15 are ultrasonically-seamed to each other and a waist-opening and a pair of leg-openings are thereby defined as shown in FIG. 1.

Figure 3:
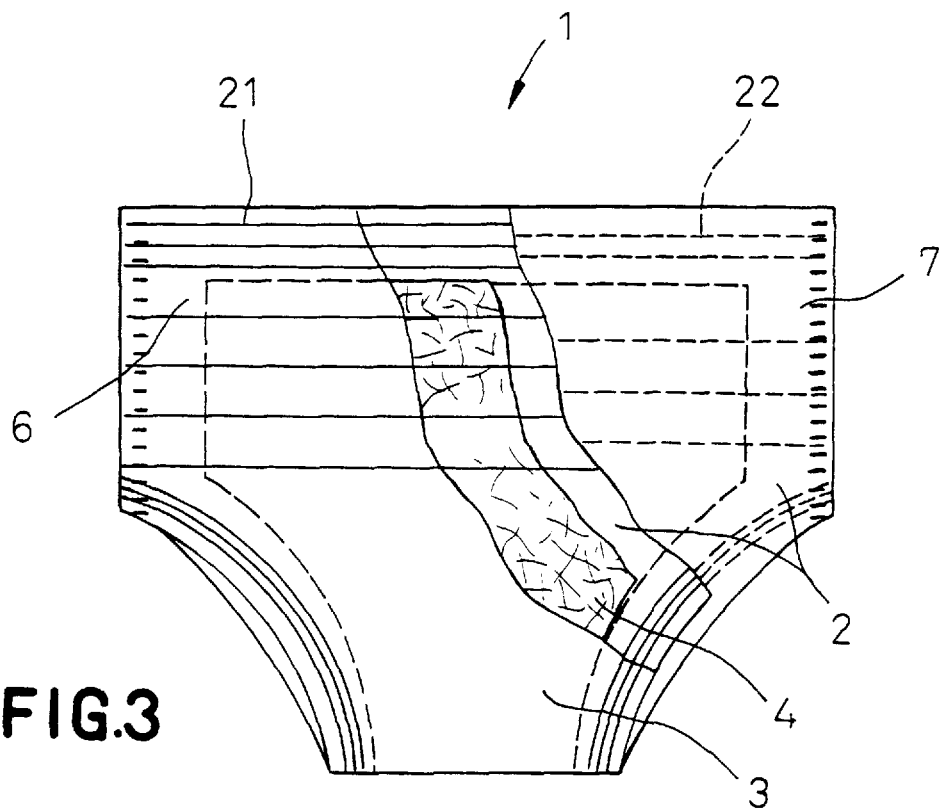
FIG. 3 is a plan view of the diaper shown by FIG. 1 as partially broken away.

FIG. 3 is a schematic plan view partially broken away of the same diaper shown in FIG. 1, exemplarily illustrating how the elastic members 21, 22 on the respective waist regions are arranged. According to the embodiment illustrated in FIG. 3, the elastic members 21 on the front waist region 6 are indicated by solid lines and the elastic members 22 on the rear waist region 7 are indicated by broken lines. A plurality of elastic members 21 extend transversely parallel one to another and a plurality of elastic members 22 also extend transversely parallel to one another but alternate with the plurality of elastic members 21, respectively. The respective elastic members 21, 22 arranged in this manner do not overlap each other as the diaper 1 is folded in two and thereby the side edges 12, 14; 13, 15 of the diaper can be maintained in a relatively planar and smooth state not only before but also after being subjected to ultrasonic-seaming. The side edges 12, 14; 13, 15 which are planar prior to the ultrasonic-seaming facilitate the mutually facing side edges to be closely placed one upon another.

Figure 4:
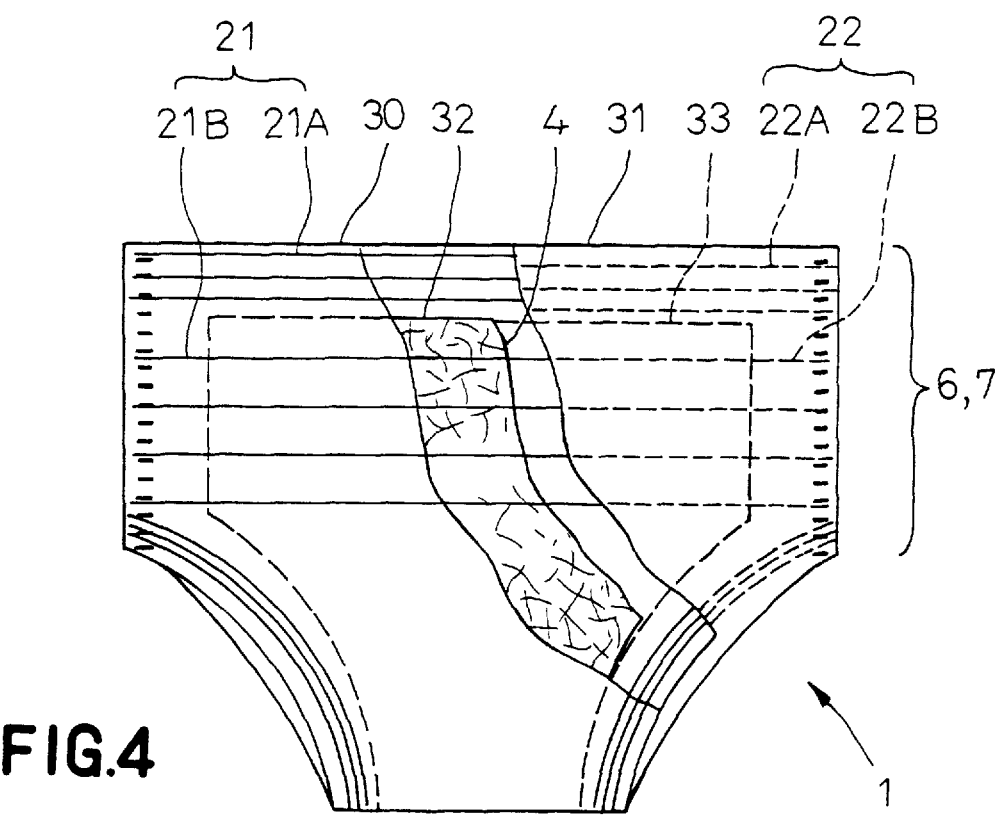
FIG. 4 is a view similar to FIG. 3 showing another embodiment of the inventive diaper.

FIG. 4 is a view similar to FIG. 3 showing another embodiment of the invention. According to this embodiment of the diaper 1, of the elastic members 21, 22 on the respective waist regions, elastic members 21A, 22A arranged in front and rear end regions 10, 11 defined between the front and rear ends 30, 31 of the front and rear waist regions 6, 7 and longitudinally opposite ends 32, 33 of the liquid-absorbent core 4 lying in the front and rear waist regions 6, 7, respectively, extend transversely so as to alternate one with another longitudinally of the diaper 1 without being overlapped one by another. On the other hand, elastic members 21B, 22B transversely extending on the front and rear waist regions 6, 7 across the core 4 below the longitudinally opposite ends 32, 33 do overlap one another. It is a common practice in making the diaper to employ a relatively wide and thick elastic member as each of the elastic members 21A, 22A in order to assure relatively high elasticity adjacent the waist-opening and to employ a relatively narrow and thin elastic member, which has a relatively low elasticity, as each of the elastic members 21B, 22B. So far as the width as well as the thickness of each of the respective elastic members are appropriately selected, the object of the invention is satisfactorily achieved even when the elastic members 21, 22 are arranged to partially overlap one another, as in the embodiment illustrated by FIG. 4.

Figure 5:
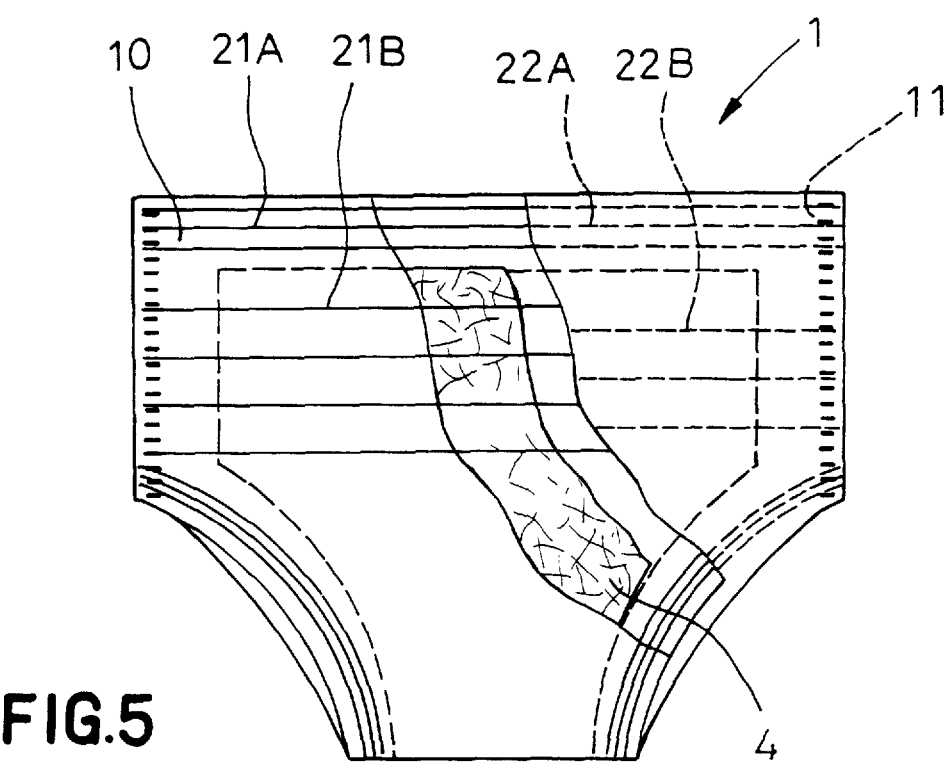
FIG. 5 is a view similar to FIG. 3 showing still another embodiment of the inventive diaper.

FIG. 5 is a view similar to FIG. 3 showing still another embodiment of the invention. With the diaper 1 according to this embodiment, the elastic members 21A, 22A extending along the longitudinally opposite ends 10, 11 of the diaper 1 overlap one another but the elastic members 21B, 22B extending across the core 4 alternate with one another longitudinally of the diaper 1.

To implement the invention, nonwoven fabric, perforated plastic film or the like may be used as material for the topsheet 2 and nonwoven fabric, plastic film or the like may be used as material for the backsheet 3 of the diaper 1. The liquid-absorbent core 4 may be formed, for example, by fluff pulp or a mixture of such fluff pulp and superabsortive particles. The respective elastic members 21, 22, 23 may be selected from those having desired cross-sectional shapes and elasticities and their attachment to the topsheet 2 and the backsheet 3 may be preferably achieved with hot melt type adhesive. Joining or bonding of the remaining components of the diaper 1 may be achieved by, in addition to use of appropriate adhesive agents such as hot melt type adhesive, heat-sealing techniques if the components to be bonded are of a heat-sealable nature.

What is claimed is:

1. A disposable absorbent pants type undergarment comprising a liquid-permeable topsheet, a liquid-impermeable backsheet and a liquid-absorbent core disposed therebetween to form a front region, a rear region and a crotch region therebetween, the front and rear waist regions being spaced from each other along a longitudinal axis of the undergarment and with the topsheet being located inside said undergarment and joined together along transversely opposite side edges thereof to define a waist-opening and a pair of leg-openings provided with a plurality of elastic members extending circumferentially parallel to one another and spaced apart one from another along the longitudinal axis, wherein:

said elastic members are arranged such that, between adjacent ones of elastic members provided on one of the front and rear waist regions, elastic members provided on the other of the front and rear waist regions are respectively interposed within said side edges to reduce side edge thickness.

2. The undergarment according to claim 1, wherein said arranged elastic members lie within regions defined between longitudinally opposite ends of the front and rear regions and longitudinally opposite ends of the core, respectively.

3. The undergarment according to claim 1, wherein the arranged elastic members extend across the liquid-absorbent core.

4. The undergarment according to claim 1, wherein each of the elastic members lying within regions defined between longitudinally opposite ends of the front and rear regions and longitudinally opposite ends of the core, respectively are formed with a width and thickness to define a high elasticity, and each of the elastic members extending across the liquid-absorbent core are formed with a width and thickness to define a lower elasticity.

5. The undergarment according to claim 1, wherein said side edges are ultrasonically sealed together.

* * * * *